(12) United States Patent
McVeigh et al.

(10) Patent No.: US 12,263,084 B2
(45) Date of Patent: *Apr. 1, 2025

(54) COMPACT PROSTHETIC HEART VALVE DEVICE

(71) Applicant: MEDTRONIC INC., Minneapolis, MN (US)

(72) Inventors: Cahal McVeigh, White Bear Township, MN (US); Jean-Pierre Dueri, Los Gatos, CA (US); Yogesh A. Darekar, Irvine, CA (US); Priya Nair, Shoreview, MN (US); Finn O. Rinne, Santa Rosa, CA (US); George N. Hallak, Costa Mesa, CA (US); Brenda L. McIntire, Walnut Creek, CA (US); Elliot J. Howard, San Carlos, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/716,699

(22) Filed: Apr. 8, 2022

(65) Prior Publication Data

US 2022/0226112 A1 Jul. 21, 2022

Related U.S. Application Data

(63) Continuation of application No. 16/853,851, filed on Apr. 21, 2020, now Pat. No. 11,318,013.

(51) Int. Cl.
*A61F 2/24* (2006.01)

(52) U.S. Cl.
CPC .......... *A61F 2/2418* (2013.01); *A61F 2/2409* (2013.01); *A61F 2210/0014* (2013.01); *A61F 2220/0008* (2013.01); *A61F 2230/0008* (2013.01); *A61F 2230/0017* (2013.01)

(58) Field of Classification Search
CPC ............................ A61F 2/2418; A61F 2/2409
See application file for complete search history.

(56) References Cited

U.S. PATENT DOCUMENTS

| | | |
|---|---|---|
| 9,034,032 B2 | 5/2015 | Mclean et al. |
| 9,034,033 B2 | 5/2015 | Mclean et al. |
| 9,037,757 B2 | 5/2015 | Mclean et al. |
| 9,125,740 B2 | 9/2015 | Morriss et al. |
| 9,421,098 B2 | 8/2016 | Gifford, III et al. |
| 9,572,662 B2 | 2/2017 | Morriss et al. |
| 9,763,780 B2 | 9/2017 | Morriss et al. |

(Continued)

FOREIGN PATENT DOCUMENTS

| | | |
|---|---|---|
| IT | UB20155767 A1 | 5/2017 |
| WO | 2018157177 A1 | 8/2018 |

OTHER PUBLICATIONS

Extended European Search Report, EP Application No. 22214670.6, mailed May 24, 2023.

(Continued)

*Primary Examiner* — Suba Ganesan
(74) *Attorney, Agent, or Firm* — Medler Ferro Woodhouse & Mills PLLC

(57) ABSTRACT

The devices and methods of this disclosure relate to a heart valve prosthesis that is configured to be implanted within a native heart valve having a smaller perimeter annuli with a generally elliptical shape.

13 Claims, 10 Drawing Sheets

(56) References Cited

U.S. PATENT DOCUMENTS

| | | |
|---|---|---|
| 9,901,443 B2 | 2/2018 | Morriss et al. |
| 10,111,747 B2 | 10/2018 | Gifford, III |
| 10,238,490 B2 | 3/2019 | Gifford, III et al. |
| 10,702,378 B2 | 7/2020 | Miyashiro |
| 10,729,541 B2 | 8/2020 | Francis et al. |
| 10,786,352 B2 | 9/2020 | Francis et al. |
| 2010/0094411 A1 | 4/2010 | Tuval et al. |
| 2011/0313515 A1 | 12/2011 | Quadri et al. |
| 2012/0215303 A1 | 8/2012 | Quadri et al. |
| 2015/0328002 A1* | 11/2015 | McLean ............... A61F 2/2418 623/2.36 |
| 2016/0367360 A1 | 12/2016 | Cartledge |
| 2017/0325948 A1 | 11/2017 | Wallace |
| 2018/0055629 A1* | 3/2018 | Oba .................... A61F 2/2418 |
| 2018/0296335 A1* | 10/2018 | Miyashiro ........... A61F 2/2418 |
| 2019/0328525 A1 | 10/2019 | Noe et al. |
| 2019/0336280 A1 | 11/2019 | Naor |
| 2020/0100897 A1 | 4/2020 | Mclean et al. |
| 2021/0338419 A1* | 11/2021 | Gifford, III .......... A61F 2/2409 |

OTHER PUBLICATIONS

Extended European Search Report dated Sep. 14, 2021 in EP Appl. No. 21 168 810.6.

* cited by examiner

COMPACT PROSTHETIC HEART VALVE DEVICE

CROSS-REFERENCE TO RELATED APPLICATION

The present application is a continuation of prior U.S. application Ser. No. 16/853,851, filed Apr. 21, 2020, now U.S. Pat. No. [TBD], which is incorporated by reference herein in its entirety.

FIELD

The present technology is generally related to prosthetic heart valve devices, and in particular is directed to prosthetic heart valve devices for percutaneous repair and/or replacement of native mitral valves.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a radially compressed configuration so that the valve prosthesis can be advanced through the patient's vasculature. Once positioned at the treatment site, the valve prosthesis can be expanded to engage tissue at the diseased heart valve region to, for instance, hold the valve prosthesis in position.

While these valve prostheses offer minimally invasive methods for heart valve repair and/or replacement, challenges remain to providing heart valve prostheses for patients with smaller native heart valves than the general population, for example, due to either having a smaller adult stature than the general population, or to being a child or adolescent. In an adult patient population that may benefit from a mitral valve prosthesis for treating mitral regurgitation, for instance, as many as 7% may be screened out due to having native mitral valves with annulus perimeters of between 89 mm to 101 mm that are currently considered too small to accept known mitral valve prostheses, which are sized for implantation within native mitral valves having annulus perimeters of between 101 mm to 119 mm. Such native mitral valves having smaller perimeter annuli tend to be more elliptical in shape, than native mitral valves having larger perimeter annuli, resulting in currently known mitral valve prostheses also being unsuitable for implantation within the smaller perimeter annuli due to those prostheses being substantially oversized in the anterior to posterior direction.

Accordingly, there is a need for a mitral valve prosthesis that may be percutaneously delivered and deployed at the site of a diseased mitral valve in a patient with a native mitral valve that is too small to accept known mitral valve prosthesis.

SUMMARY

The devices and methods of this disclosure generally relate to a heart valve prosthesis that is configured to be implanted within a native heart valve having a smaller perimeter annuli with a generally elliptical shape.

In one aspect, the present disclosure provides a heart valve prosthesis that includes a valve support with upstream and downstream segments relative to blood flow through a native heart valve of a human heart. The upstream segment of the valve support is configured to support a prosthetic valve component and defines an inflow end of the valve support having a first outer diameter. The downstream segment of the valve support defines an outflow end of the valve support having a second outer diameter that is greater than the first outer diameter. The heart valve prosthesis further includes an anchor element that surrounds the valve support. A plurality of connectors form a downstream portion of the anchor element, the plurality of connectors being angled inward toward the valve support to be attached to the outflow end of the valve support. The anchor element is spaced from the upstream segment of the valve support to mechanically isolate the upstream segment of the valve support from the anchor element.

In another aspect, which may be combined with any of the other aspects noted herein, the disclosure provides a heart valve prosthesis with a first outer diameter of an upstream segment of a valve support that is constant from a first end of the upstream segment, which defines an inflow end of the valve support, to a second end of the upstream segment.

In another aspect, which may be combined with any of the other aspects noted herein, the disclosure provides a heart valve prosthesis with a downstream end of an upstream segment of a valve support that is adjacent a upstream end of a downstream segment of the valve support, such that the upstream end of the downstream segment has a first outer diameter and a longitudinally opposite downstream end of the downstream segment, which defines an outflow end of the valve support, has a second outer diameter that is greater than the first outer diameter.

In another aspect, which may be combined with any of the other aspects noted herein, the disclosure provides a heart valve prosthesis with a downstream segment of a valve support that is flared outwardly from a first end to a second end thereof, with the first end of the downstream segment having a first outer diameter and the second end of the downstream segment, which defines an outflow end of the valve support, having a second outer diameter that is greater than the first outer diameter.

In another aspect, which may be combined with any of the other aspects noted herein, the disclosure provides a heart valve prosthesis with an upstream segment of a valve support that tapers from a first end of the upstream segment having a first outer diameter, which defines an inflow end of the valve support, to a second end of the upstream segment having a second outer diameter that is smaller than the first outer diameter.

In another aspect, which may be combined with any of the other aspects noted herein, the disclosure provides a heart valve prosthesis with an upstream segment of a valve support tapered inwardly from upstream to downstream ends thereof such that the downstream end of the upstream segment of a valve support, with a first outer diameter, is adjacent to an upstream end of a downstream segment of the valve support with the first outer diameter. The downstream segment is flared outwardly from the upstream end to a downstream end thereof, with the downstream end of the downstream segment, which defines an outflow end of the valve support, having a second outer diameter that is larger than the first outer diameter.

In another aspect, which may be combined with any of the other aspects noted herein, the disclosure provides a heart valve prosthesis with a tissue fixation ring that forms an upstream portion of an anchor element, the tissue fixation ring being configured to engage heart tissue at or below a native annulus of the native heart valve.

In another aspect, which may be combined with any of the other aspects noted herein, the disclosure provides a heart valve prosthesis with an anchor element having a tissue fixation ring that is radially spaced from an upstream segment of a valve support a distance S in an undeployed state. The tissue fixation ring being configured to be at least partially deformable into a non-circular shape to adapt to a shape of an implantation site in a deployed state, such that the tissue fixation ring does not make contact with the upstream segment of the valve support, and thereby mechanically isolates the upstream segment of the valve support from the anchor element when implanted in vivo.

In another aspect, which may be combined with any of the other aspects noted herein, the disclosure provides a heart valve prosthesis with a plurality of connectors of an anchor element that are angled inward from a tissue fixation ring of the anchor element.

In another aspect, which may be combined with any of the other aspects noted herein, the disclosure provides a heart valve prosthesis with a plurality of connectors of an anchor element that are angled inward from a tissue fixation ring of the anchor element, the plurality of connectors being configured to flex upward, after implantation, to accommodate any radial expansion of the tissue fixation ring caused by an increase in size of an implantation site, such as a native annulus, that may occur after deployment.

In another aspect, which may be combined with any of the other aspects noted herein, the disclosure provides a heart valve prosthesis with an anchor element having a tissue fixation ring that includes one or more cleats extending outward from the tissue fixation ring to engage heart tissue upon implantation.

In another aspect, which may be combined with any of the other aspects noted herein, the disclosure provides a heart valve prosthesis with a prosthetic valve component disposed within an upstream segment of a valve support such that valve leaflets of the prosthetic valve component open into a downstream segment of the valve support during diastole.

In another aspect, which may be combined with any of the other aspects noted herein, the disclosure provides a heart valve prosthesis with a prosthetic valve component disposed within an upstream segment of a valve support such that valve leaflets of the prosthetic valve component achieve an open state having an effective orifice area greater than about 1.6 $cm^2$ during diastole.

In another aspect, which may be combined with any of the other aspects noted herein, the disclosure provides a heart valve prosthesis with a frame having a valve support that is formed of a stent-like structure having one of honeycomb-shaped and closed diamond-shaped cells.

In another aspect, which may be combined with any of the other aspects noted herein, the disclosure provides a heart valve prosthesis with a frame having an anchor element that is formed of a stent-like structure having diamond-shaped cells.

In another aspect, which may be combined with any of the other aspects noted herein, the disclosure provides a heart valve prosthesis with an outflow end of a valve support being attached, by a plurality of rivets, to a plurality of connectors of an anchor element.

In another aspect, which may be combined with any of the other aspects noted herein, the disclosure provides a heart valve prosthesis with an anchor element provided with a plurality of connectors, with each of the connectors having an inwardly curved substantially V-shape.

In another aspect, which may be combined with any of the other aspects noted herein, the disclosure provides a heart valve prosthesis with a first outer diameter and a second outer diameter. In an embodiment, the first outer diameter at an outflow end of the heart valve prosthesis is about 30 mm and the second outer diameter at an upstream end of an anchor element is about 36 mm, such that the heart valve prosthesis is sized for implantation within a patient having a smaller native annulus.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of the treatment of heart valves such as the pulmonary, aortic, mitral, or tricuspid valve, the invention may also be used in any other body passageways where it is deemed useful. Furthermore, there is no intention to be bound by any expressed or implied theory presented in the preceding technical field, background, brief summary or the following detailed description.

Prosthetic heart valve devices and methods described herein provide a heart valve replacement device that is sized to fit within a native mitral valve that is screened as too small, and likely too elliptically-shaped, to accept known mitral valve prosthesis. In accordance with embodiments hereof, the prosthetic heart valve devices may be configured for implantation within native mitral valves with annulus perimeters of between about 89 mm to about 101 mm. The prosthetic heart valve devices described herein have the requisite flexibility to adapt and conform to such native mitral valve anatomy while mechanically isolating a prosthetic heart valve from an anchoring portion of the device, particularly addressing oversizing that may occur in the anterior-posterior direction of an elliptically-shaped, smaller native mitral valve. The prosthetic heart valve devices described herein effectively absorb the distorting forces applied by the native anatomy with sufficient structural strength and integrity to withstand the dynamic conditions of the heart over time. The prosthetic heart valve devices described herein are further configured to be delivered in a less-invasive transcatheter procedure.

Figure 1:
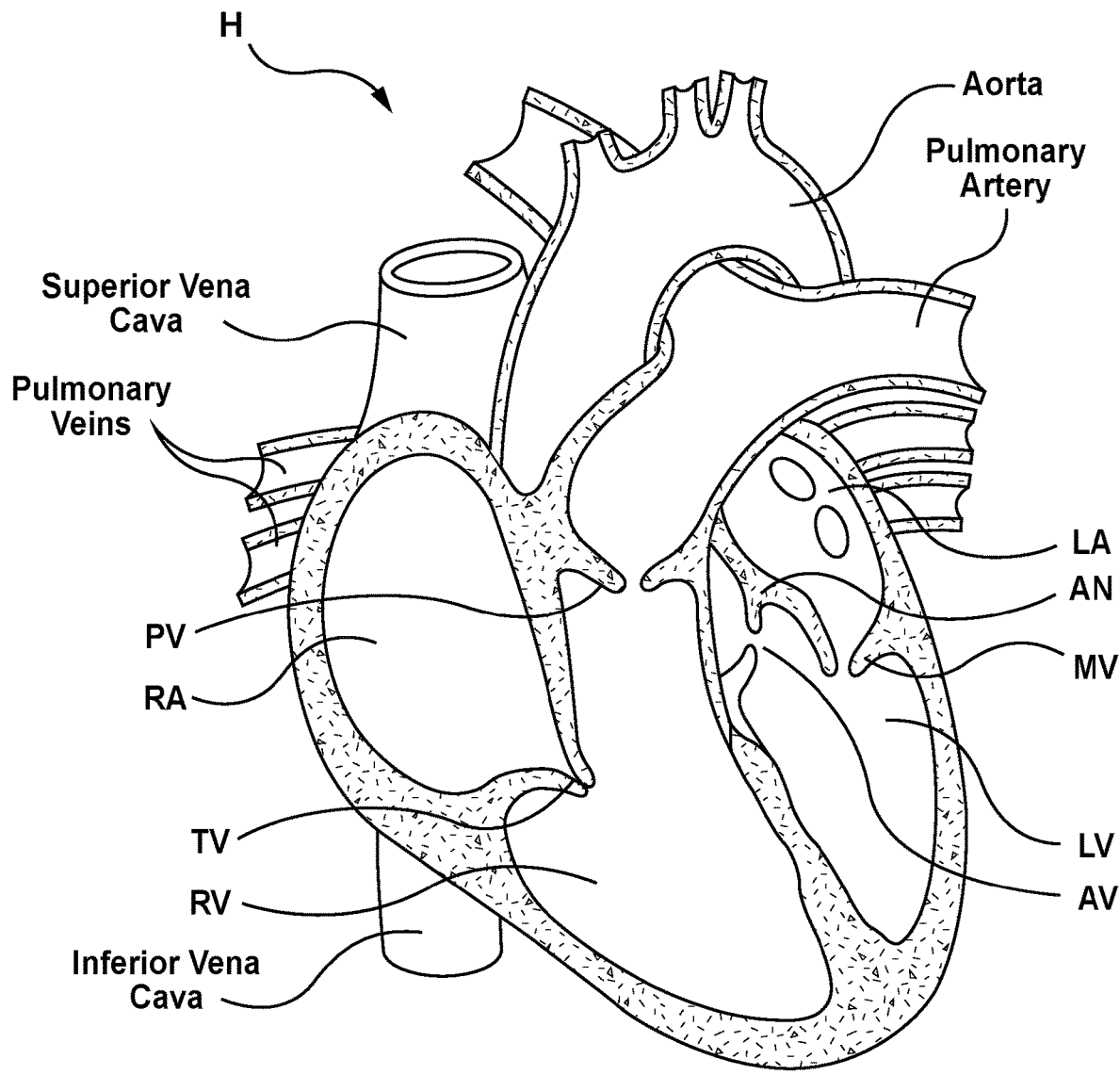
FIG. 1 depicts a schematic sectional illustration of a heart having native valve structures.

FIG. 1 is a schematic sectional illustration of a heart H that depicts the four heart chambers (right atria RA, right ventricle RV, left atria LA, left ventricle LV) and native valve structures (tricuspid valve TV, mitral valve MV, pulmonary valve PV, aortic valve AV). FIG. 2 is a schematic sectional illustration of a left ventricle LV of a heart H showing anatomical structures and a native mitral valve MV. Referring to FIGS. 1 and 2 together, the heart H comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, the valve leaflets LF of the mitral valve MV meet evenly at the free edges or "coapt" to close and prevent back flow of blood during contraction of the left ventricle LV. Referring to FIG. 2, the valve leaflets LF attach the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral valve leaflets LF are connected to papillary muscles PM, which extend upwardly from the lower wall of the left ventricle LV and the interventricular septum IVS, via branching tendons called chordae tendineae CT. In a heart H having a mitral valve MV in which the valve leaflets LF do not sufficiently coapt or meet, leakage from the left ventricle LV into the left atrium LA will occur. Several structural defects can cause the mitral valve leaflets LF to prolapse in this manner, and subsequent regurgitation to occur, including ruptured chordae tendineae CT, impairment of papillary muscles PM, e.g., due to ischemic heart disease, and enlargement of the heart and/or mitral valve annulus AN, e.g., cardiomyopathy.

Figure 2A:
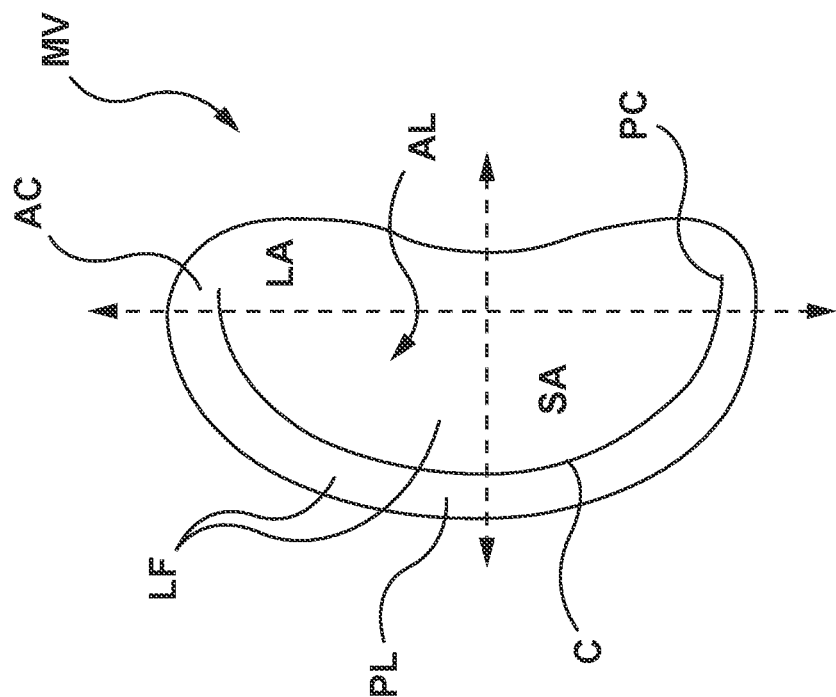
FIG. 2A depicts a schematic illustration of a native mitral valve of a heart showing normal closure of native mitral valve leaflets.
Figure 2:
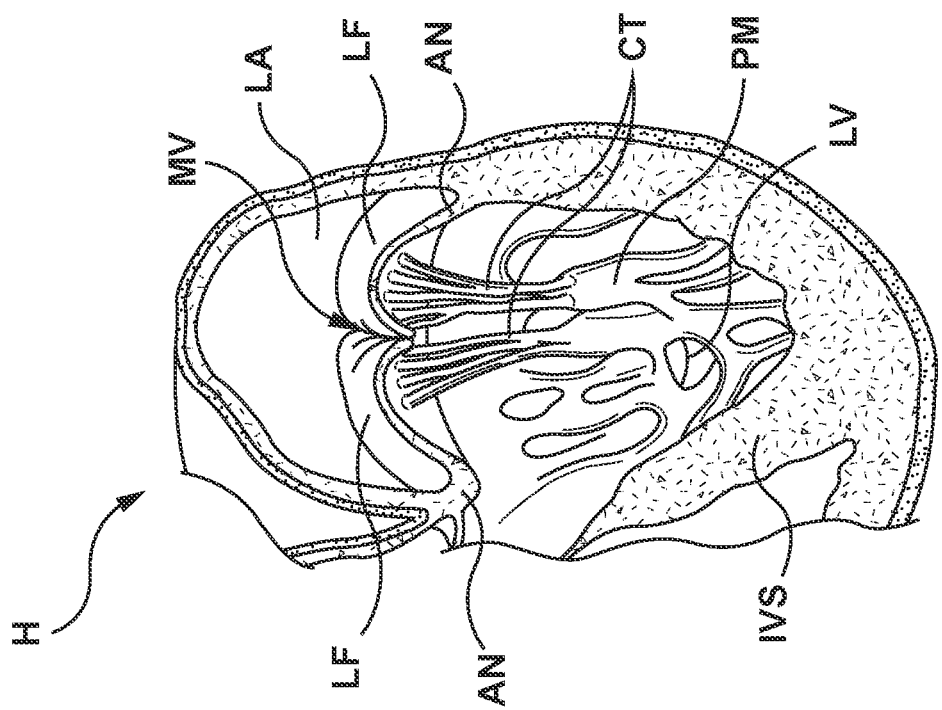
FIG. 2 depicts a schematic sectional illustration of a left ventricle of a heart showing anatomical structures and a native mitral valve.

FIG. 2A further illustrates the shape and relative sizes of valve leaflets LF of a mitral valve MV, and it may be seen that the overall valve has a generally "D"-shape or kidney-like shape with a long axis LA and a short axis SA. The line of coaptation C of the valve leaflets LF is curved or C-shaped, thereby defining a relatively large anterior leaflet AL and substantially smaller posterior leaflet PL. Both valve leaflets appear generally crescent-shaped from the superior or atrial side, with the anterior leaflet AL being substantially wider in the middle of the valve than the posterior leaflet. As illustrated in FIG. 2A, the valve leaflets LF join together at corners called the anterolateral commissure AC and posteromedial commissure PC, respectively, at the opposing ends of the line of coaptation C.

For healthy adult humans, with reference to the long axis LA and the short axis SA shown in FIG. 2A, the long axis LA is typically within a range from about 33.6±6.0 mm to about 42.2±2.6 mm, with a standard deviation in a range of 2.6 mm to 6.0 mm, and the short axis SA is typically within a range from about 23.8±4.0 mm to about 33.7±3.5 mm, with a standard deviation in a range of 2.2 mm to 4.0 mm. However, with adult patients having decreased mitral valve function these values can be larger, for example, LA can be within a range from about 38.5±3.2 mm to about 52.7±3.9 mm, with a standard deviation in a range of 2.9 mm to 6.0 mm, and SA can be within a range from about 26.7±2.8 mm to about 37.2±0.4 mm, with a standard deviation in a range of 0.4 mm to 6.4 mm. For a patient population with diseased smaller native mitral valves to be treated with the prosthetic heart valve devices described herein, these values may be, for example, LA within a range from about 30 mm to 34 mm and SA within a range from about 24 mm to about 32 mm.

Figure 3:
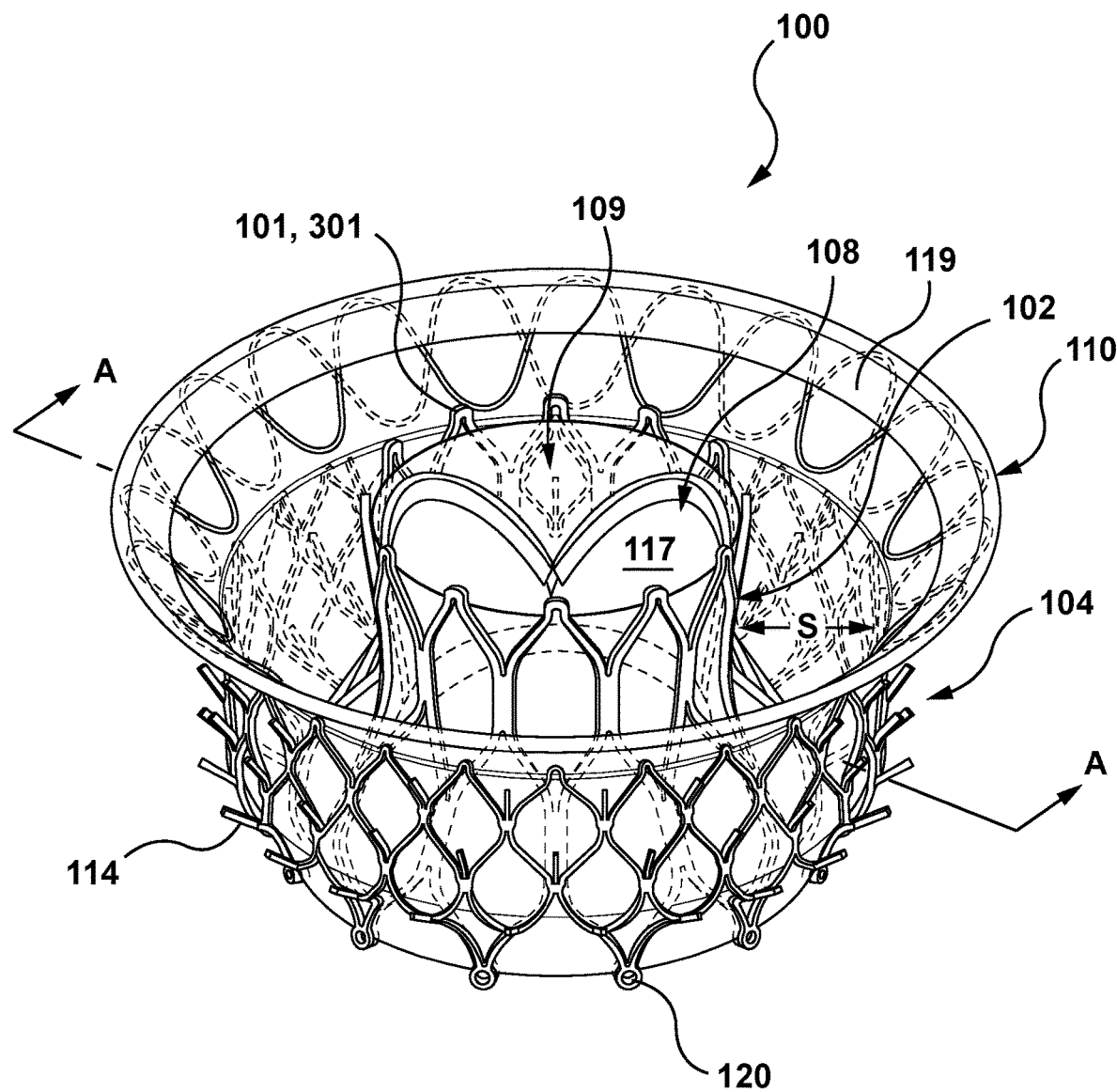
FIG. 3 depicts a perspective view of a heart valve prosthesis in accordance with an aspect of the disclosure.
Figure 3A:
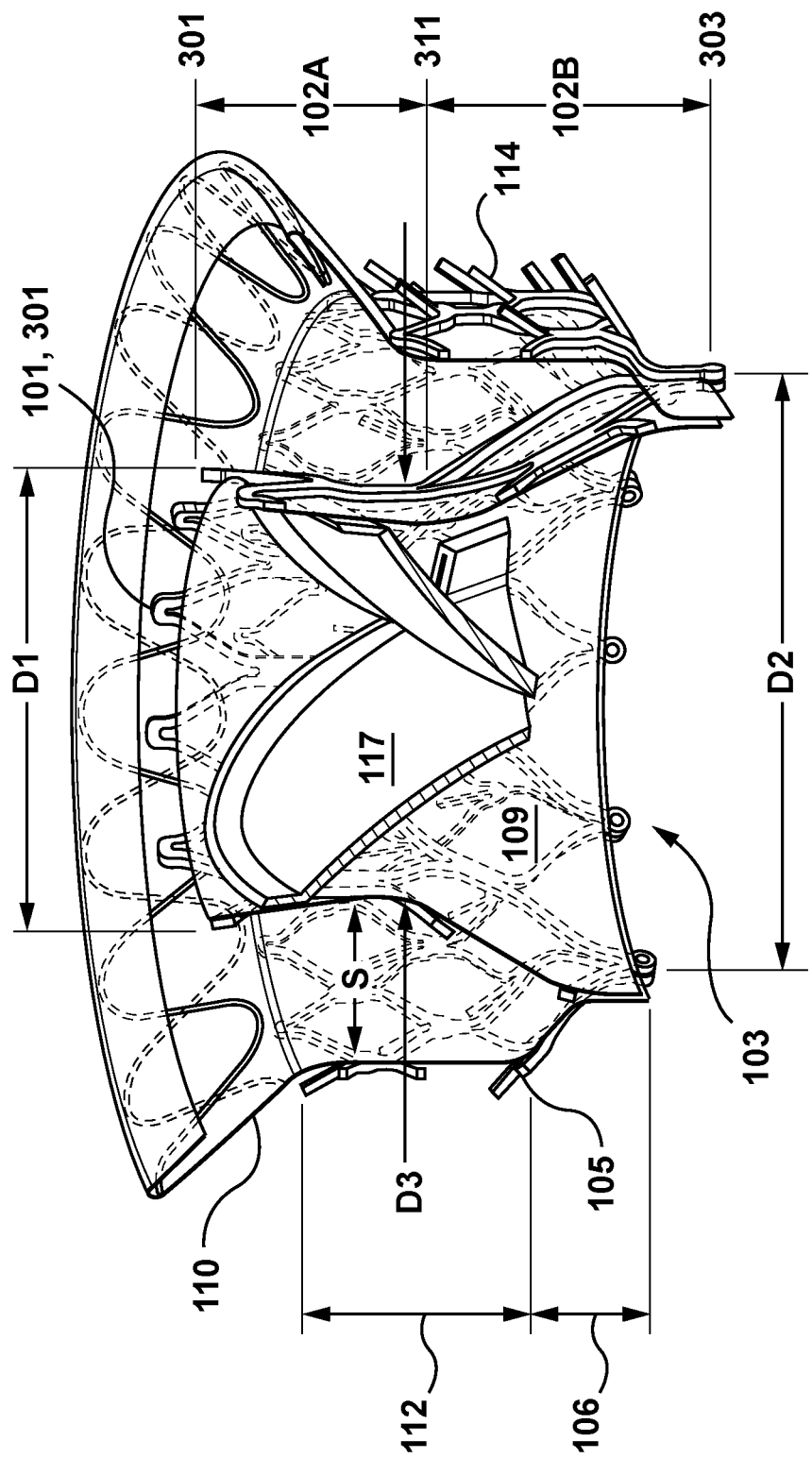
FIG. 3A depicts a sectional view of the heart valve prosthesis of FIG. 3, taken along line A-A thereof.

A perspective view of a heart valve prosthesis 100 in accordance with an aspect of the disclosure is shown in FIG. 3, and a sectional view of the heart valve prosthesis 100, taken along line A-A of FIG. 3, is shown in FIG. 3A. The heart valve prosthesis 100 is configured to be compressed into a reduced-diameter delivery configuration (not shown) and to return to an expanded, deployed configuration, as shown in FIG. 3A. In accordance with embodiments hereof, when in the delivery configuration, the heart valve prosthesis 100 has a low profile suitable for delivery to and deployment within a native mitral valve via a suitable delivery catheter that may be tracked to the deployment site of the native mitral valve of a heart via any one of a transseptal, retrograde, or transapical approach.

In an aspect of the disclosure, the heart valve prosthesis 100 includes a valve support 102 at least partially surrounded by an anchor element 104. The valve support 102 is a hollow stent-like structure that defines a lumen 109 from an inflow end 101 of the valve support 102 to an outflow end 103 of the valve support 102. In an aspect of the disclosure, the valve support 102 has a first or upstream segment 102A and a second or downstream segment 102B, with "upstream" and "downstream" referring to intended deployed positions of the respective segments within a native mitral valve of a heart relative to blood flow therethrough.

The upstream segment 102A of the valve support 102 is configured to support a prosthetic valve component 108 therein, which will be described in more detail below. The upstream segment 102A may be described as having a substantially cylindrical shape with a first or upstream end 301 of the upstream segment 102A defining the inflow end 101 of the valve support 102. A second or downstream end 311 of the upstream segment 102A of the valve support 102 is coextensive with a first or upstream end 311 of the downstream segment 102B of the valve support 102, and a second or downstream end 303 of the downstream segment 102B defines the outflow end 103 of the valve support 102.

In an aspect of the disclosure, the first end 301 of the upstream segment 102A that defines the inflow end 101 of the valve support 102 has an outer diameter D1, and the second end 303 of the downstream segment 102B that defines the outflow end 103 of the valve support 102 has an outer diameter D2 that is greater than the outer diameter D1. In various aspects of the disclosure, the second end 311 of the upstream segment 102A and the coextensive first end 311 of the downstream segment 102B have an outer diameter D3 that may be equal to or less than the outer diameter D1.

In an embodiment of a valve support 102 in which an outer diameter D1 and an outer diameter D3 are equal to each other, the outer diameter D1 of the upstream segment 102A may be described as being constant along the entire length of the upstream segment 102A from the first end 301 to the second end 311 thereof. In such an embodiment, the outer diameter D3 of the coextensive first end 311 of the downstream segment 102B is also equal to the outer diameter D1, such that the downstream segment 102B is flared outwardly from the outer diameter D1 at its first end 311 to the outer diameter D2 at its second end 303, with the outer diameter D2 being greater than the outer diameter D1 as stated above. In an aspect of the disclosure, an upstream segment 102A having a constant outer diameter D1 along its entire length may be described to have the form of a hollow, substantially cylindrical shape, and a downstream segment 102B that flares radially, outwardly from a first end 311 having the outer diameter D1 to a second end having the outer diameter D2 may be described to have the form of a hollow, substantially frustoconical shape. In another aspect, an upstream segment 102A having a constant outer diameter D1 along its entire length may be described to have the form of a hollow, substantially cylindrical shape, and a downstream segment 102B that flares radially, outwardly from a first end 311 having the outer diameter D1 to a second end having the outer diameter D2 may be described to have the form of a hollow, substantially trumpet shaped.

In an embodiment of a valve support 102 in which an outer diameter D3 is less than an outer diameter D1, an upstream segment 102A gradually tapers along its length from its first end 301 having the outer diameter D1 to its second end 311 having the outer diameter D3. In an aspect of the disclosure, a valve support 102 having a tapered inflow profile may improve hemodynamics as the tapered inflow profile may promote transvalvular blood flow and reduce the possibility of paravalvular leakage. In the aforementioned embodiment, the coextensive first end 311 of the downstream segment 102B also has the outer diameter D3 that is less than the outer diameter D1, such that the downstream segment 102B is flared radially, outwardly from the outer diameter D3 at its first end 311 to the outer diameter D2 at its second end 303, with the outer diameter D2 being greater than the each of the outer diameters D1 and D3.

In an aspect of the disclosure, an anchor element 104 of a heart valve prosthesis 100 is configured to mechanically isolate an upstream segment 102A of a valve support 102 from the anchor element 104 when the heart valve prosthesis 100 is deployed within a smaller, substantially elliptically shaped native mitral valve annulus. In an aspect of the disclosure, the anchor element 104 is a hollow, stent-like structure that includes a tissue fixation ring 112 and a plurality of connectors 106. The tissue fixation ring 112 is a substantially cylindrically-shaped structure that is configured to engage heart tissue at or below an annulus of a native heart valve, such as an annulus of a native mitral valve. The tissue fixation ring 112 may be configured to engage subannular tissue, such as inward-facing surfaces of the valve leaflets, as shown in FIG. 4A. The tissue fixation ring 112 functions as an anchor for the heart valve prosthesis 100 to secure its deployed position within a native annulus. In an aspect of the disclosure, the tissue fixation ring 112 includes one or more cleats or prongs 114 that extend outward from an exterior side of the tissue fixation ring 113 to engage heart tissue. In another aspect of the disclosure, a tissue fixation ring 113 may employ barbs, spikes, or other tissue fixation mechanisms for engaging heat tissue.

In an aspect of the disclosure, the tissue fixation ring 112 is radially spaced from the upstream segment 102A of the valve support 102 a distance S in an undeployed state, as shown in FIGS. 3 and 3A, and is at least partially deformable into a non-circular shape to adapt to a shape of an implantation site in a deployed state, such as deforming into a substantially elliptical shape when deployed within a smaller native mitral valve annulus. In an aspect of the disclosure, a tissue fixation ring 112 and an upstream segment 102A of a valve support 102 are sized relative to each other to provide a distance S therebetween so as to be configured to prevent contact therebetween, when the heart valve prosthesis is deployed, and to thereby mechanically isolate the upstream segment 102A of the valve support 102 from the anchor element 104.

Figure 4:
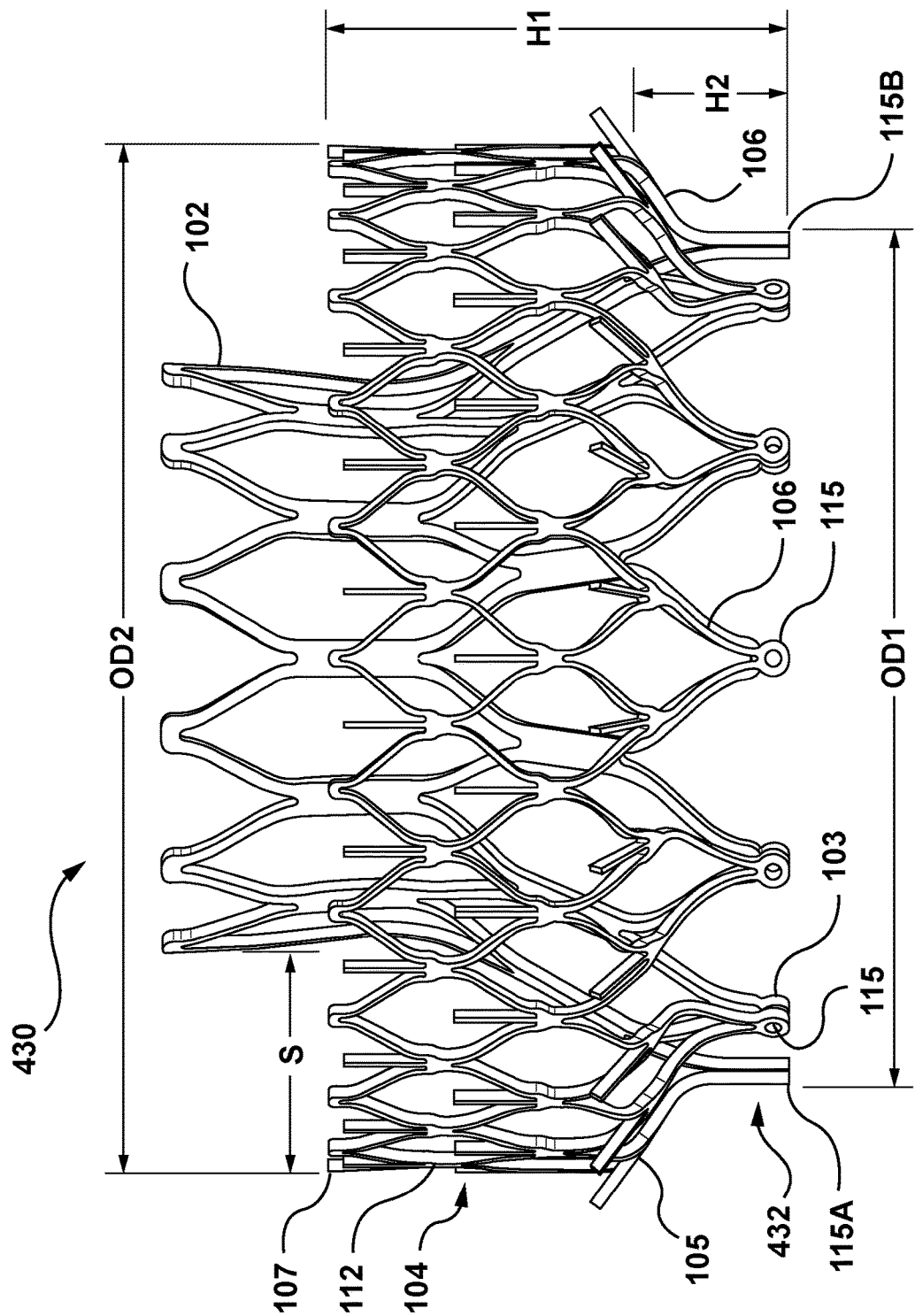
FIG. 4 depicts a side view of a frame of a heart valve prosthesis in an undeployed state in accordance with an aspect of the disclosure.
Figure 4A:
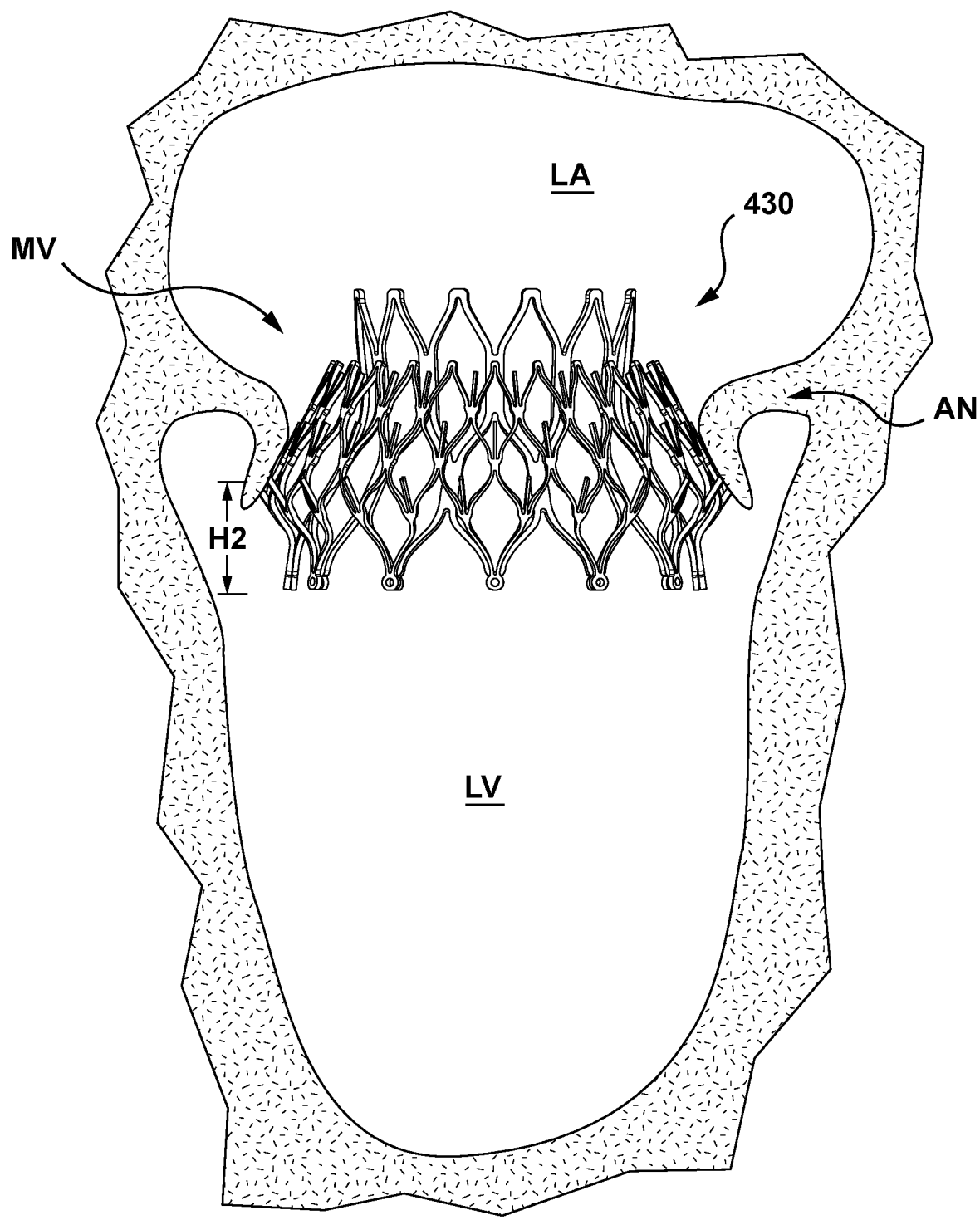
FIG. 4A depicts a side view of the frame of FIG. 4 in a deployed state in accordance with an aspect of the disclosure.

With reference to FIGS. 3, 3A and 4, the plurality of connectors 106 are angled radially inward from a downstream end 105 of the tissue fixation ring 112 to attach to the outflow end 103 of the valve support 102. In an aspect of the disclosure, an outflow end 103 of the valve support 102 may be attached to downstream ends 115 of the plurality of connectors 106 by a plurality of rivets 120. In other aspects of the disclosure, the valve support 102 and the plurality of connectors 106 of the fixation ring 112 may be coupled to each other by any of a variety of methods known in the art that, by way of example and not limitation, may include suturing, soldering, welding, staples, or other fasteners, mechanical interlocking, snap fit, friction or interference fit, or any combination thereof.

Each of the connectors 106 of the fixation ring 112 may be described as having an inwardly curved, substantially V-shape with downstream ends 115 of the plurality of connectors 106 being respective vertices of the V-shape. In an aspect of the disclosure, the plurality of connectors 106 may be formed by inwardly curving or bending downstream portions, or downstream halves, of a last row of cells of the stent-like structure of the anchor element 104. In an aspect of the disclosure, the plurality of connectors 106 may extend radially inwardly and downwardly from respective upstream ends, which are coextensive with the downstream end 105 of the tissue fixation ring, to the respective downstream ends 115 thereof and are so configured to permit upward flexion of the plurality of connectors 106, after implantation, to accommodate any radial expansion of the tissue fixation ring 112 that may occur after deployment due to an increase in size of the native annulus, which may occur, for example, due to tissue remodeling after valve replacement, natural growth until adulthood, and/or potential disease progression.

FIG. 4 depicts a frame 430 of a heart valve prosthesis 100 in accordance with an embodiment hereof, the frame 430 including a valve support 102 and an anchor element 104. In the embodiment of FIG. 4, the valve support 102 of the frame 430 is formed of a stent-like structure having honeycomb-shaped cells and the anchor element 104 of the frame 430 is formed of a stent-like structure having closed diamond-shaped cells. In another embodiment shown in FIG. 5, each of a valve support 502 and an anchor element 104 of a frame 530 is formed of a stent-like structure having closed diamond-shaped cells.

In an aspect of the disclosure with reference to FIG. 4, an outer diameter OD1 of an outflow end 432 of the frame 430 is a measurement that spans a distance between outer sides of downstream ends 115A, 115B of respective connectors 106 on opposing sides of the anchor element 104. In another aspect of the disclosure with reference to FIG. 4, an outer diameter OD2 of an upstream end 107 of the anchor element 104 is a measurement that spans a distance between outer sides of the upstream end 107 on opposing sides of the anchor element 104, and is the broadest point of the anchor element 104. In accordance with an embodiment hereof, a heart valve prosthesis 100 with a frame 430 having an outer diameter OD1 of about 30+/−0.5 mm and an outer diameter OD2 of about 36+/−0.5 mm is sized for implantation within a patient having a smaller native mitral valve annulus.

Figure 3B:
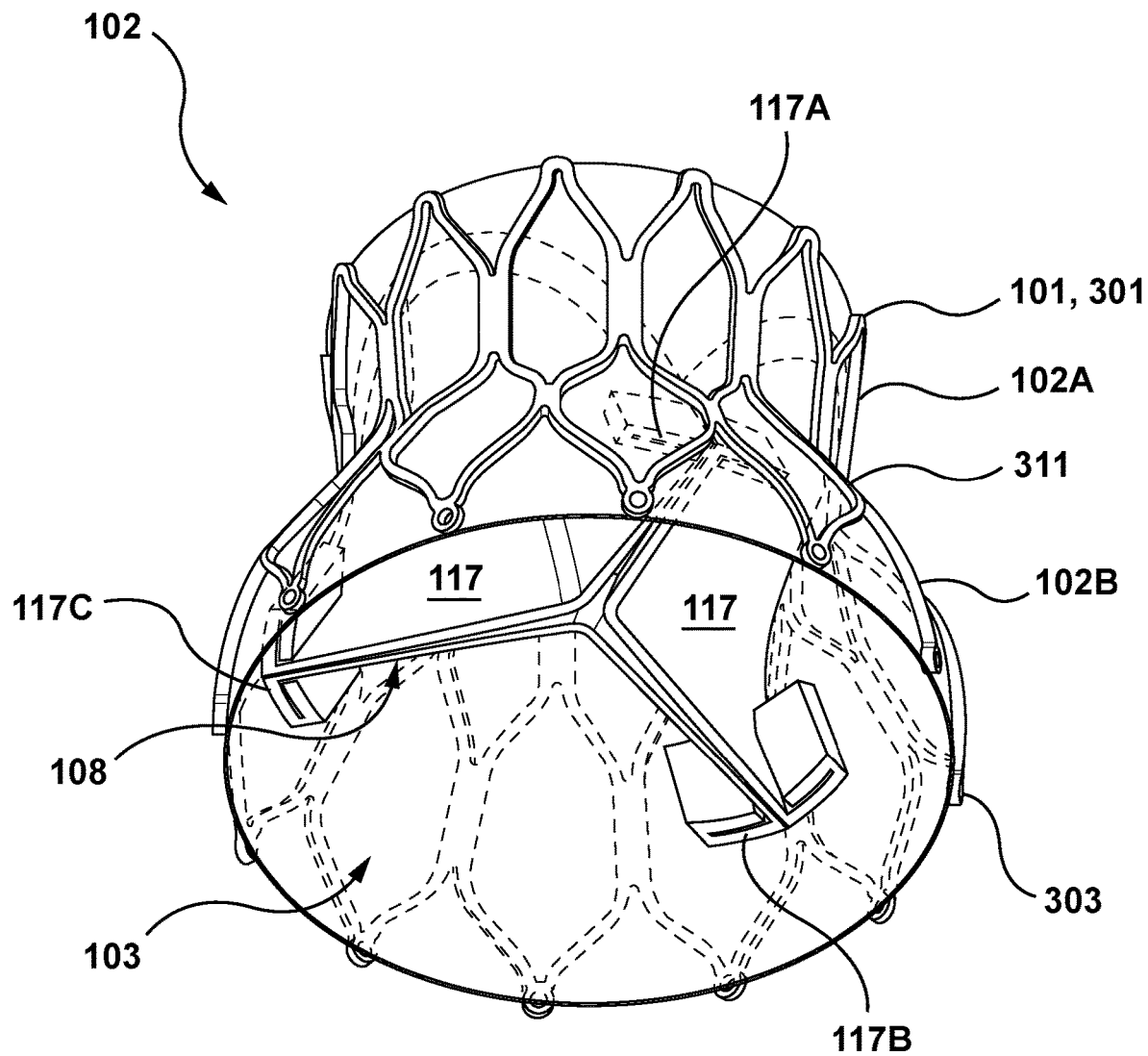
FIG. 3B depicts a perspective view of a valve support of the heart valve prosthesis of FIG. 3 with a prosthetic valve component secured therein in accordance with an aspect of the disclosure.
Figure 3D:
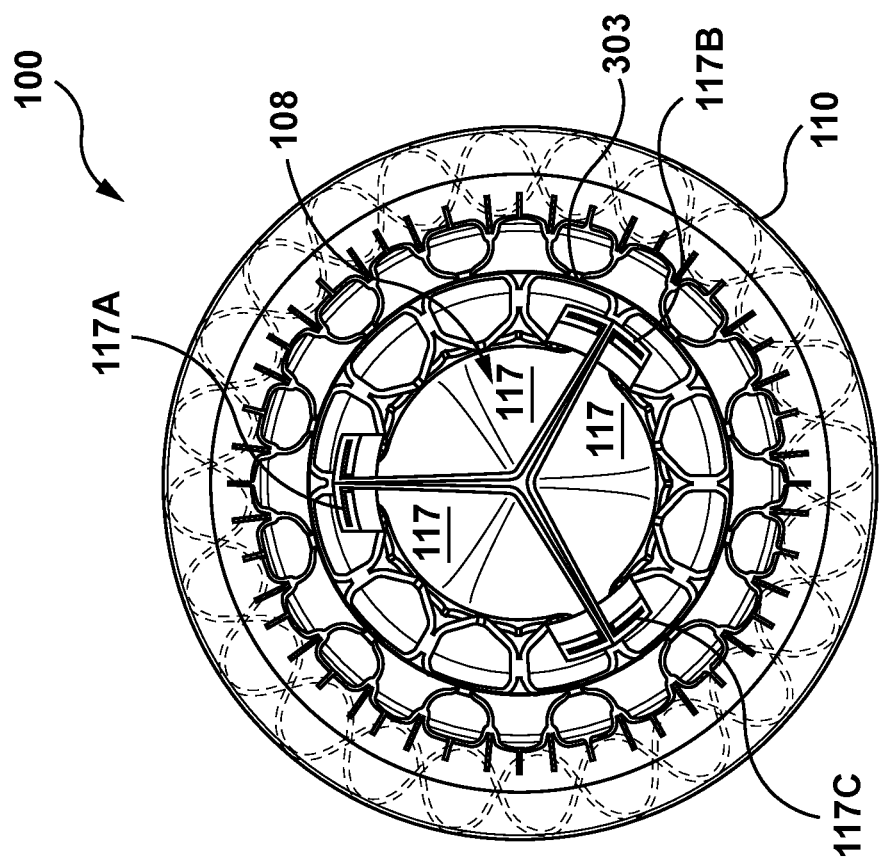
FIG. 3D depicts a ventricular view of the heart valve prosthesis shown in FIG. 3 in accordance with an aspect of the disclosure.
Figure 3C:
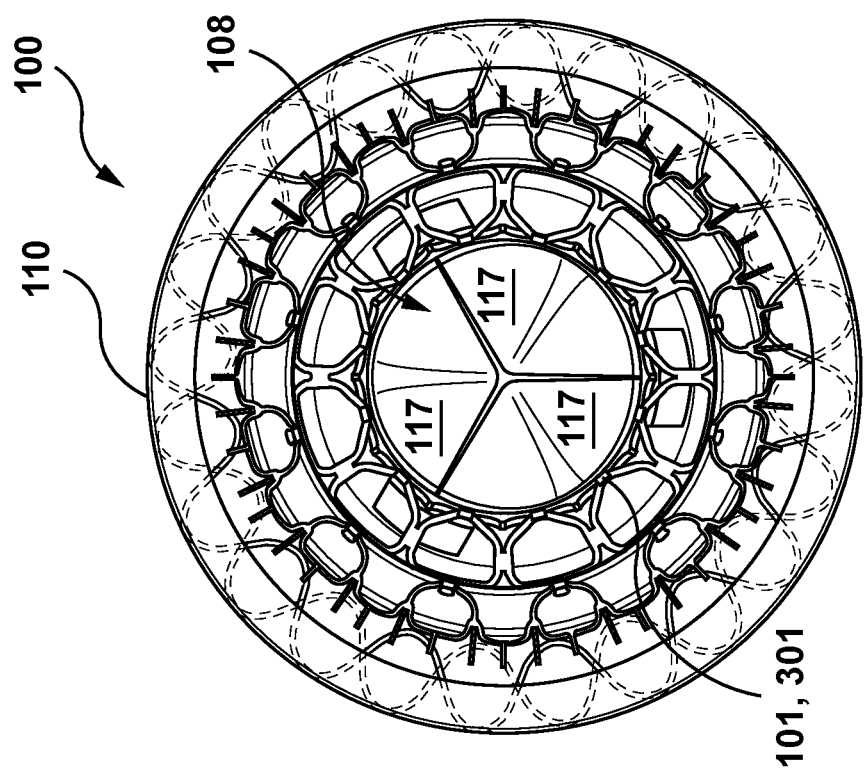
FIG. 3C depicts an atrial view of the heart valve prosthesis shown in FIG. 3 in accordance with an aspect of the disclosure.
Figure 4B:
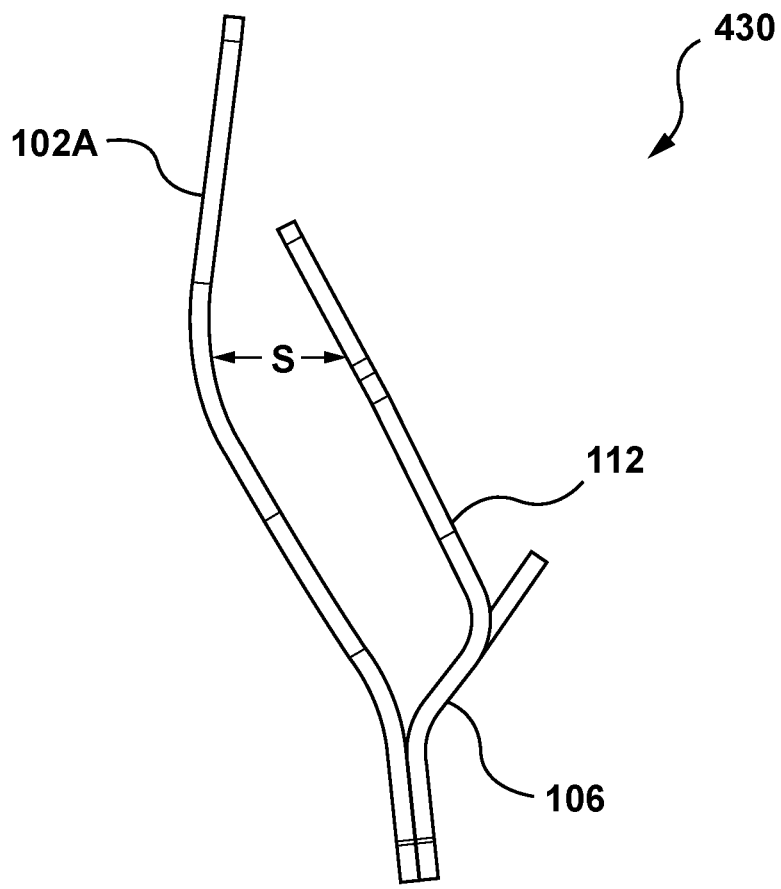
FIG. 4B depicts a sectional view of a portion of the frame of FIG. 4A in the deployed state in accordance with an aspect of the disclosure.

In addition, with reference to FIGS. 4, 4A and 4B, a frame 430 for use in compact transcatheter heart valve prostheses in accordance with embodiments hereof has a shorter overall height H1 and a reduced cone height H2 than conventional heart valve prostheses, which reduces protrusion of the compact transcatheter heart valve prostheses below a valve plane of the native mitral valve into the left ventricle. In accordance with an embodiment hereof, a heart valve prosthesis 100 with a frame 430 having a shorter overall height H1 of about 16.2 mm+/−0.5 mm and a reduced cone height H2 of about 5.4 mm+/−0.5 mm is sized for implantation within a patient having a smaller native mitral valve annulus to thereby reduce or prevent left ventricular outflow track (LVOT) obstruction. In an aspect of the disclosure despite this lower profile, the compact transcatheter heart valve prostheses perform with equivalent, or, in some cases, improved hemodynamic performance than their larger and taller counterparts. To demonstrate the benefit of the shorted overall height H1 and the reduced cone height H2, as well as other features, FIG. 4A depicts a side view of the frame 430 of FIG. 4 in a deployed state within an annulus AN of a native mitral valve MV in accordance with an aspect of the disclosure, and FIG. 4B depicts a sectional view of a portion of the frame 430 of FIG. 4A in the deployed state in accordance with an aspect of the disclosure. FIG. 4A only shows a frame 430 deployed within the mitral valve MV for ease of illustration, and one of ordinary skill in the art would readily recognize how the illustration applies to a deployed state of a compact heart valve prosthesis 100 as shown and described with reference to FIGS. 3 and 3A-3D.

A cone height H2 of the frame 430 refers to a measurement between the downstream end 105 of the tissue fixation ring 112 and the outflow end 432 of the frame 430. The cone height H2 encompasses the plurality of connectors 106 of the anchor element 104. In an aspect of the disclosure, a cone height H2 is relatively short and a remainder of the frame 430 sits at or near a valve plane of the annulus AN, with the entirety of a deployed compact heart valve prosthesis 100 being shifted upwardly toward the left atrium LA, to thereby reduce or prevent left ventricular outflow track (LVOT) obstruction. In an aspect of the disclosure, the reduced cone height H2 of the frame 430 also minimizes contact and/or interaction with chordae tendineae and the papillary muscles, and provides advantages in patients with small left ventricles, who heretofore may have been screened out from receiving a mitral valve prosthesis because their annuli are too small or because there would be too much LVOT obstruction.

As previously described above and with reference to FIGS. 4 and 4B, in an aspect of the disclosure, a tissue fixation ring 112 of a frame 430 is radially spaced from an upstream segment 102A of a valve support 102 a distance S in an undeployed state, and is at least partially deformable into a non-circular shape to adapt to a shape of the native mitral valve annulus in a deployed state. Although once deformed the distance S is reduced when the frame 430 is in the deployed state within a native mitral valve annulus, the tissue fixation ring 112 does not make contact with the upstream segment 102A of the valve support 102, as shown in FIG. 4B, and thereby mechanical isolation between the upstream segment 102A of the valve support 102 from the anchor element 104 is maintained when the compact heart valve prosthesis 100 is implanted in vivo.

A heart valve prosthesis 100 in accordance with aspects of the disclosure, and with continued reference to FIGS. 3 and 3A, includes a brim or rim element 110 that extends outwardly from the upstream end 107 of the anchor element 104. The brim element 110 includes overlapping, 180 degree out of phase sinusoidal wire forms that are attached and hinged to the anchor element 104 by a suitable biocompatible low-profile fabric 119 used in bioprosthetic implants namely endovascular grafts, heart valves or left atrial appendage devices to promote bio-integration, such as woven polyethylene terephthalate (PET) fabric. The brim element 110 may act as an atrial retainer, if present, and to serve such a function the brim element 110 may be configured to engage tissue above the native annulus AN, such as a supra-annular surface or some other tissue in the left atrium, to thereby inhibit downstream migration of a prosthetic heart valve 100, for e.g., during atrial systole.

A heart valve prosthesis 100 in accordance with aspects of the disclosure includes a prosthetic valve component 108, as previously noted above. FIG. 3B depicts a perspective view of a valve support 102 with a prosthetic valve component 108 secured therein, the valve support 102 being shown in FIG. 3B removed from the remainder of the heart valve prosthesis 100 shown in FIG. 3 for ease of illustration. FIG. 3C depicts an atrial view of the heart valve prosthesis 100 shown in FIG. 3, and FIG. 3D depicts a ventricular view of the heart valve prosthesis 100 shown in FIG. 3. The prosthetic valve component 108 includes valve leaflets 117, for e.g., three valve leaflets 117, that are disposed to coapt within the narrow upstream segment 102A of the valve support 102 with the commissures 117A, 117B, 117C of the valve leaflets 117 being secured within the wider downstream segment 102B of the valve support 102, such that the valve leaflets 117 open into the wider downstream segment 102B of the valve support 102 during diastole. In an aspect of the disclosure, the leaflet commissures 117A, 117B, 117C being arranged within the wider downstream segment 102B provides the prosthetic valve component 108 with a larger effective orifice area (EOA) by allowing the valve leaflets 117 to open more without interacting with the valve support 102. In an aspect of the disclosure, in an open state during diastole, the prosthetic valve component 108 may have an effective orifice area greater than about 1.6 $cm^2$.

The valve leaflets 117 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Figure 5:
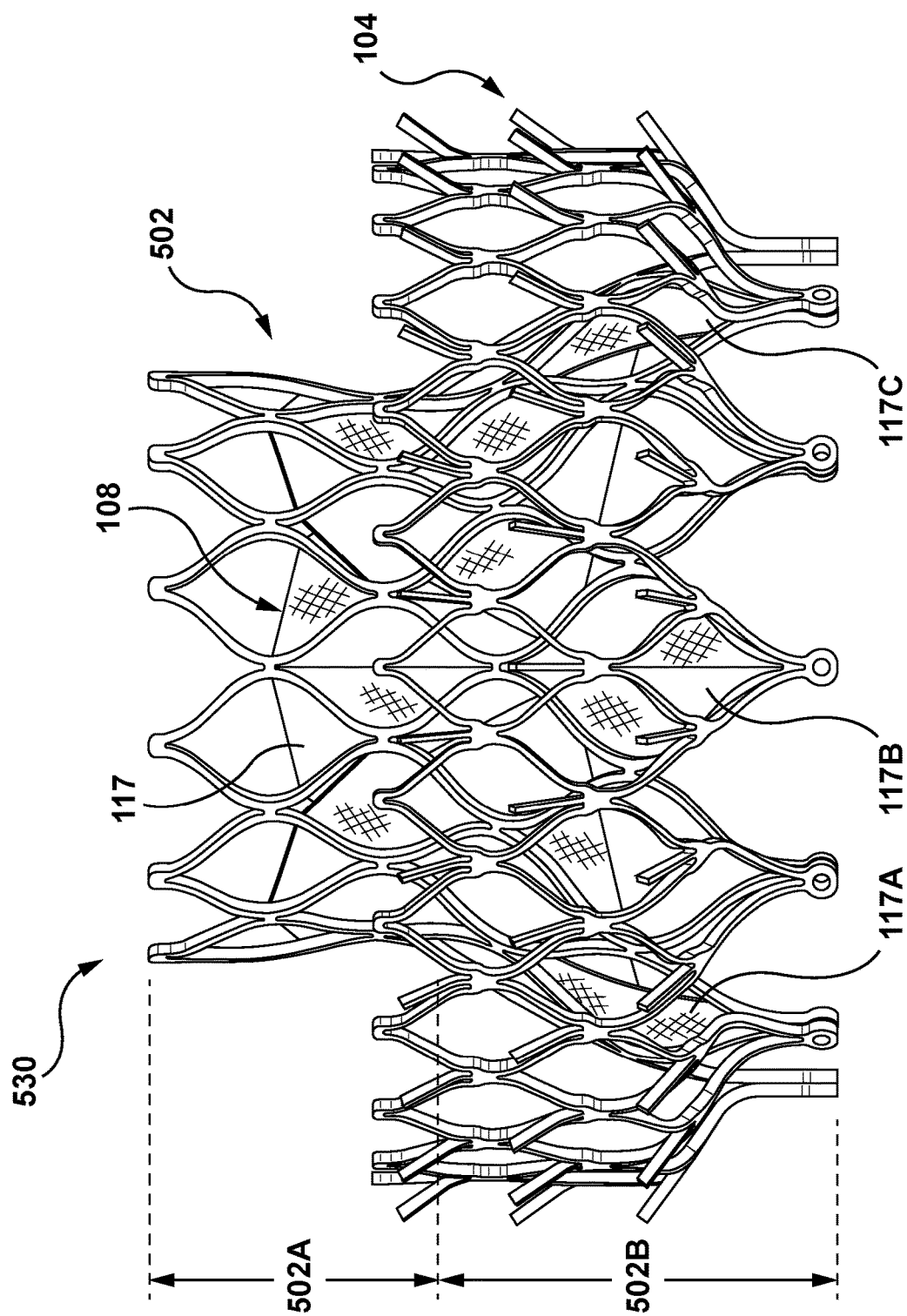
FIG. 5 depicts a side view of a frame of a heart valve prosthesis in accordance with an aspect of the disclosure.

In an aspect of the disclosure, FIG. 5 depicts a prosthetic valve component 108 secured within a valve support 502 of a frame 530. The valve component 108 includes valve leaflets 117 being disposed to coapt within a narrow upstream segment 502A of the valve support 502 and the commissures 117A, 117B, 117C of the valve leaflets 117 being secured within a wider downstream segment 502B of the valve support 502, such that the valve leaflets 117 open into the wider downstream segment 502B of the valve support 502 during diastole.

In an aspect of the disclosure, a valve support 102 and a tissue fixation ring 112 may be fully lined by a low-profile fabric 119 designed to provide sealing, such as that used in bioprosthetic implants namely endovascular grafts, heart valves or left atrial appendage devices to promote bio-integration, such as woven polyethylene terephthalate (PET) fabric. In an aspect of the disclosure, a woven textile may be employed that will act as a platform for subsequent tissue ingrowth. In an aspect of the disclosure, a low-profile fabric 119 for attaching to the valve support 102 and the tissue fixation ring 104 may be two separate pieces or types of fabric in order to mitigate leaks and reduce manufacturing time.

Any of a frame, valve support, tissue fixation ring, plurality of connectors, etc. described herein as an element of a heart valve prothesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide a heart valve prothesis 100 that is configured to be compressed into a reduced-diameter delivery configuration for transcatheter delivery to a native valve, whereby release from a delivery catheter returns the prosthesis to an expanded, deployed configuration.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A heart valve prosthesis having a radially compressed state for delivery to a deployment site and a radially expanded, deployed state for deployment at the deployment site, comprising:
   a valve support having a first segment and a second segment,
      the first segment configured to support a prosthetic valve component therein and defining a first end of the valve support having a first outer diameter, and
      the second segment defining a second end of the valve support having a second outer diameter that is greater than the first outer diameter; and
   an anchor element that surrounds the valve support, the anchor element having a plurality of connectors that are angled inward toward the valve support and are attached to the valve support, wherein the anchor element is attached to the valve support in both the radially compressed state prior to delivery to the deployment site and the radially expanded, deployed state,
   wherein the second end of the valve support having the second diameter is disposed radially within the anchor element,
   wherein the first segment has a first end that defines the first end of the valve support and a second end that is adjacent a first end of the second segment, and
   wherein the second segment is flared outwardly from the first end to a second end thereof, with the first end of the second segment having the first outer diameter such that the first segment is substantially cylindrical and the second end of the second segment, which defines the second end of the valve support, having the second outer diameter.

2. The heart valve prosthesis of claim 1, wherein the anchor element includes a tissue fixation ring configured to engage heart tissue at or below a native annulus of the native heart valve.

3. The heart valve prosthesis of claim 2, wherein the tissue fixation ring is at least partially deformable into a non-circular shape to adapt to a shape of the implantation site in the radially expanded, deployed state.

4. The heart valve prosthesis of claim 2, wherein the plurality of connectors are angled inward from the tissue fixation ring.

5. The heart valve prosthesis of claim 1, further comprising a prosthetic valve component disposed within the first segment of the valve support such that valve leaflets of the prosthetic valve component open into the second segment of the valve support during diastole.

6. The heart valve prosthesis of claim 1, wherein the valve support and the anchor element comprise a frame of the heart valve prosthesis.

7. A heart valve prosthesis of claim 1, wherein the heart valve prosthesis is configured for implantation within a native heart valve positioned between an atrium and a ventricle.

8. The heart valve prosthesis of claim 7, wherein the anchor element further includes a tissue fixation ring coupled to the connectors, the connectors extend inward from the tissue fixation ring, wherein the tissue fixation ring has a cone height measured between a lower end of the tissue fixation ring and an end of the connectors opposite the fixation ring.

9. The heart valve prosthesis of claim 1, wherein an end of the anchor element is attached to the second end of the valve support.

10. The heart valve prosthesis of claim 9, wherein the second end of the valve support is a downstream end of the valve support, and wherein the end of the anchor element attached to the downstream end of the valve support is a downstream end of the anchor element.

11. The heart valve prosthesis of claim 1, wherein:
the first segment of the valve support is an upstream segment of the valve support;
the second segment of the valve support is a downstream segment of the valve support;
the first end of the valve support is an inflow end of the valve support; and
the second end of the valve support is an outflow end of the valve support.

12. A heart valve prosthesis having a radially compressed state for delivery to a deployment site and a radially expanded, deployed state for deployment at the deployment site, comprising:
a valve support having an upstream segment and a downstream segment relative to blood flow through a native heart valve of a human heart,
the upstream segment configured to support a prosthetic valve component therein and defining an inflow end of the valve support-having a first outer diameter, and
the downstream segment defining an outflow end of the valve support having a second outer diameter that is greater than the first outer diameter; and
an anchor element that surrounds the valve support, the anchor element having a tissue fixation ring and a plurality of connectors that are angled inward from the tissue fixation ring toward the valve support and are attached to the valve support, wherein the anchor element is attached to the valve support in both the radially compressed state prior to delivery to the deployment site and the radially expanded, deployed state,
wherein the outflow end of the valve support having the second diameter is disposed radially within the anchor element,
wherein the heart valve prosthesis is configured for implantation within a native heart valve positioned between an atrium and a ventricle,
the tissue fixation ring has a cone height measured between a lower end of the tissue fixation ring and an outflow end of the connectors,
wherein the valve support and the anchor element together form a frame, wherein the cone height is shorter than a height of a remainder of the frame such that the remainder of the frame is configured to sit at or near a valve plane of an annulus of the native heart valve, thereby the entirety of the heart valve prosthesis in the radially expanded, deployed state is configured to sit upwardly toward the atrium to reduce or prevent obstruction of the ventricle.

13. A heart valve prosthesis having a radially compressed state for delivery to a deployment site and a radially expanded, deployed state for deployment at the deployment site, comprising:
a valve support having an upstream segment and a downstream segment relative to blood flow through a native heart valve of a human heart,
the upstream segment configured to support a prosthetic valve component therein and defining an inflow end of the valve support having a first outer diameter, and
the downstream segment defining an outflow end of the valve support having a second outer diameter that is greater than the first outer diameter; and
an anchor element that surrounds the valve support, the anchor element having a plurality of connectors that are angled inward toward the valve support and are attached to the valve support, wherein the anchor element is attached to the valve support in both the radially compressed state prior to delivery to the deployment site and the radially expanded, deployed state,
wherein the tissue fixation ring has a cone height measured between a lower end of the tissue fixation ring and an outflow end of the connectors,
wherein an overall height of the frame is 16.2 mm+/−0.5 mm and the cone height of the frame is 5.4 mm+/−0.5 mm.

* * * * *